United States Patent [19]

Kikuchi et al.

[11] Patent Number: 4,958,001

[45] Date of Patent: Sep. 18, 1990

[54] DICYCLOHEXYL-3,4,3',4'-TETRACARBOXYLIC ACID OR DIANHYDRIDE THEREOF AND POLYAMIDE-ACID AND POLYIMIDE OBTAINED THEREFROM

[75] Inventors: Tohru Kikuchi; Toshiyuki Fujita; Takayuki Saito; Mitsumasa Kojima; Hidetaka Sato; Hiroshi Suzuki, all of Hitachi, Japan

[73] Assignee: Hitachi Chemical Company, Ltd., Tokyo, Japan

[21] Appl. No.: 252,608

[22] Filed: Oct. 3, 1988

[30] Foreign Application Priority Data

Oct. 8, 1987 [JP] Japan .................. 62-254049
Dec. 17, 1987 [JP] Japan .................. 62-319206
May 10, 1988 [JP] Japan .................. 63-112967

[51] Int. Cl.$^5$ ............................................. C08G 69/26
[52] U.S. Cl. ................................ 528/346; 428/1; 549/465

[58] Field of Search .............. 528/346; 549/465; 428/1

[56] References Cited

U.S. PATENT DOCUMENTS 2,931,789  4/1960  Wielicki ..................... 528/346

*Primary Examiner*—Maurice J. Welsh
*Attorney, Agent, or Firm*—Antonelli, Terry, Stout & Kraus

[57] ABSTRACT

A polyimide obtained from a polyamide-acid or polyamide-acid ester prepared by reacting dicyclohexyl-3,4,3', 4'-tetracarboxylic acid or dianhydride with a diamine is excellent in transparency, heat resistance and mechanical properties, said polyimide being able to be obtained at a lower temperature, and particularly suitable for an orientation film used in a liquid crystal display device.

11 Claims, 6 Drawing Sheets

DICYCLOHEXYL-3,4,3',4'-TETRACARBOXYLIC ACID OR DIANHYDRIDE THEREOF AND POLYAMIDE-ACID AND POLYIMIDE OBTAINED THEREFROM

BACKGROUND OF THE INVENTION

This invention relates to dicyclohexyl-3,4,3',4'-tetracarboxylic acid or dianhydride thereof, a process for producing the same, a polyamide-acid or polyamide-acid ester and polyimide obtained therefrom, and a process for producing the same.

Heretofore, polyimides are produced by reacting a diamine with a tetracarboxylic dianhydride in a solvent to produce a polyamide-acid, which is then subjected to dehydration and ring closure, or directly obtained by reacting a diisocyanate with a tetracarboxylic dianhydride. The thus obtained polyamide-acids and polyimides show various properties depending on the selection and combination of diamines, diisocyanates, and tetracarboxylic dianhydrides used to give, for example, those excellent in heat resistance, those rich in flexibility, those excellent in solubility, and the like.

Among them, a polyimide obtained by using an aromatic tetracarboxylic dianhydride as a tetracarboxylic dianhydride is excellent in heat resistance and mechanical properties, but is disadvantageous in that the temperature of 300° C. or higher is necessary for the synthesis and the obtained polyimide has a brown appearance.

On the other hand, polyimides have been applied to various fields, for example, to optical devices, e.g. orientation films in liquid crystal display devices. When the polyimide obtained by using an aromatic tetracarboxylic dianhydride is to be applied to a liquid crystal display device, since heat resistance of the liquid crystal display device itself is poor, the device itself is decomposed during the step of polyimidization. Further, such a polyimide is low in transparency, so that the application of it to the liquid crystal display device is very difficult.

In contrast, it is known that aliphatic tetracarboxylic dianhydrides such as 1,2,3,4-butanetetracarboxylic dianhydride, or alicyclic tetracarboxylic dianhydrides such as 1,2,4,5-cyclohexyltetracarboxylic dianhydride, and 1,2,3,4-cyclopentanetetracarboxylic dianhydride can provide polyimides good in transparency by a low temperature polyimidization. But the polyimides obtained by using the aliphatic tetracarboxylic dianhydrides have a defect in that the heat resistance is very low. Further, polyimides obtained by using 1,2,4,5-cyclohexyltetracarboxylic dianhydride which is an alicyclic tetracarboxylic acid have higher glass transition temperature and pyrolysis beginning temperature than polyimides obtained by using the aliphatic tetracarboxylic dianhydride but are very brittle. On the other hand, when 1,2,3,4-cyclopentanetetracarboxylic dianhydride is used, the polymerization degree of polyamide-acid is not enhanced, and thus the resulting polyimide is very brittle.

SUMMARY OF THE INVENTION

The present invention provides dicyclohexyl-3,4,3',4'-tetracarboxylic acid or dianhydride thereof and a process for producing the same, which can yield a polyimide having good transparency, heat resistance and mechanical properties by low-temperature polyimization.

The present invention also provides a polyamide-acid or an ester thereof obtained by reacting dicyclohexyl-3,4,3',4'-tetracarboxylic acid or dianhydride thereof with a diamine.

The present invention further provides a polyimide obtained from said polyamide-acid or an ester thereof.

The present invention still further provides a liquid crystal display device using such a polyimide as an orientation film.

DESCRIPTION OF THE PREFERRED EMBODIMENTS

Figure 1:
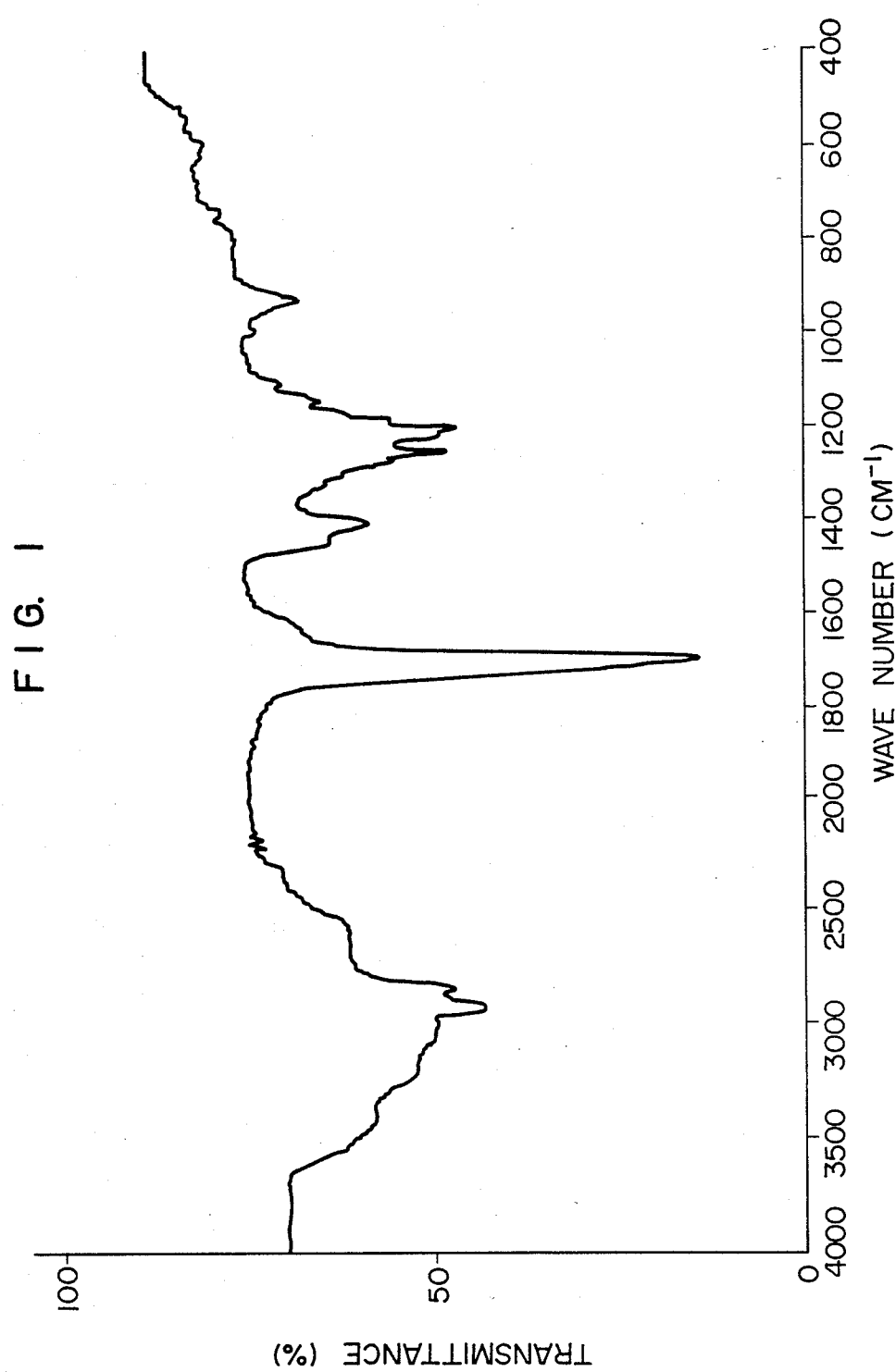
FIG. 1 is an infrared spectrum of dicyclohexyl-3,4,3',4'-tetracarboxylic acid.

Dicyclohexyl-3,4,3',4'-tetracarboxylic acid is a compound represented by the formula:

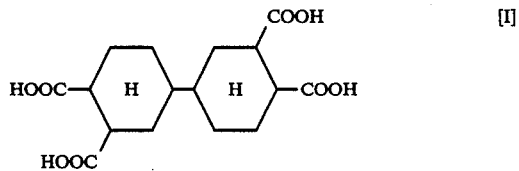

Further, dicyclohexyl-3,4,3',4'-tetracarboxylic dianhydride is a compound represented by the formula:

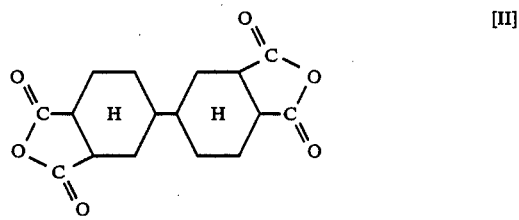

The compound of the formula [I] can be produced by hydrogenation of biphenyl-3,4,3',4'-tetracarboxylic acid tetramethyl ester using a rhodium catalyst, followed by hydrolysis.

The compound of the formula [II] can be produced by dehydration ring closure of dicyclohexyl-3,4,3',4'-tetracarboxylic acid obtained above.

These processes mentioned above are explained in detail below.

Biphenyl-3,4,3',4'-tetracarboxylic acid tetramethyl ester is white crystals having a melting point of 102° to 103° C. Therefore, in order to carry out the hydrogenation, it is dissolved in an organic solvent. As the organic solvent, there can be used any solvents which can dissolve biphenyl-3,4,3',4'-tetracarboxylic acid tetramethyl ester and do not bring about side reactions during the hydrogenation.

Examples of the organic solvent are alcohols such as methanol, ethanol, isopropanol, etc.; esters such as methyl acetate, ethyl acetate, etc.; ethers such as tetrahydrofuran, diethyl ether, diisopropyl ether, etc.; alkanes such as n-hexane, cyclohexane, etc. The amount of the solvent used is not particularly limited and is suitable for dissolving biphenyl-3,4,3',4'-tetracarboxylic acid tetramethyl ester under the reaction conditions.

As the catalyst for hydrogenation, there can be used a metallic rhodium powder or a rhodium catalyst carried on an activated carbon, alumina, diatomaceous earth, silica, etc. The amount of catalyst is usually 2 to 50% by weight based on the weight of biphenyl-3,3,4,3',4'-tetracarboxylic acid tetramethyl ester, and is changed depending on the amount of rhodium carried on a carrier.

The hydrogen pressure during the reaction is usually 2 to 100 kg/cm$^2$, preferably 20 to 50 kg/cm$^2$. When the hydrogen pressure is too low, there is a tendency to prolong the reaction time, while when the hydrogen pressure is too high, there is a tendency to make the control of the reaction temperature difficult due to too rapid reaction rate.

The reaction temperature is usually from room temperature to 150° C., preferably 50° to 120° C. When the reaction temperature is too low, there is a tendency to prolong the reaction time. On the other hand, when the reaction temperature is higher than 150° C., the carbonyl group of the ester is attacked to easily produce by-products.

Under the above-mentioned suitable reaction conditions, the reaction is completed in 30 minutes to 20 hours. The progress of the reaction or the end of the reaction can be judged by reading a pressure gauge to obtain the consumed amount of hydrogen.

After completion of the reaction, the catalyst is separated from the reaction mixture by filtration. Further, the solvent is removed by evaporation to give dicyclohexyl-3,4,3',4'-tetracarboxylic acid tetramethyl ester.

The hydrolysis of dicyclohexyl-3,4,3',4'-tetracarboxylic acid tetramethyl ester can be carried out by a conventional method, e.g., acid hydrolysis or alkali hydrolysis, followed by acid deposition.

In the case of the acid hydrolysis, a mineral acid such as sulfuric acid, hydrochloric acid, or the like is used as a catalyst. Since dicyclohexyl-3,4,3',4'-tetracarboxylic acid tetramethyl ester is insoluble in water, it is dissolved in acetic acid previously, followed by addition to an aqueous solution containing a mineral acid catalyst. The hydrolysis is carried out under reflux with heating. Since dicyclohexyl-3,4,3',4'-tetracarboxylic acid after the hydrolysis is hardly soluble in water, it is deposited as white fine powder-like crystals, which are separated by filtration.

In the case of the alkali hydrolysis, an alkali such as sodium hydroxide, potassium hydroxide, or the like is used as a catalyst. In this case, dicyclohexyl-3,4,3',4'-tetracarboxylic acid tetramethyl ester is dissolved in methanol, followed by addition to an aqueous solution containing an alkali catalyst. The hydrolysis is carried out under reflux with heating. After completion of the reaction, since dicyclohexyl-3,4,3',4'-tetracarboxylic acid is dissolved in the aqueous solution in the form of an alkali salt, acid deposition is carried out by adding a mineral acid such as hydrochloric acid, sulfuric acid, or the like thereto to give white fine powder-like crystals.

Dehydration ring closure of dicyclohexyl-3,4,3',4'-tetracarboxylic acid to give dianhydride thereof can be carried out by a conventional process, e.g. heating under reduced pressure, or dissolving in acetic anhydride with heating followed by recrystallization.

In the case of heating under reduced pressure, the desired dianhydride can be obtained by heating at 180° to 220° C. under reduced pressure of 30 to 100 mm Hg for 1 to 5 hours.

In the case of using acetic anhydride, the desired dianhydride can be obtained by adding 12 g of acetic anhydride to 1 g of dicyclohexyl-3,4,3',4'-tetracarboxylic acid, refluxing for 1 hour, subjecting to hot filtration, and allowing to stand to deposit the crystals of dicyclohexyl-3,4,3',4'-tetracarboxylic dianhydride.

When the resulting dianhydride is reacted with an alcohol, there can be obtained dicyclohexyl-3,4,3',4'-tetracarboxylic acid diester.

The above-mentioned reactions can be represented by the following chemical formulae.

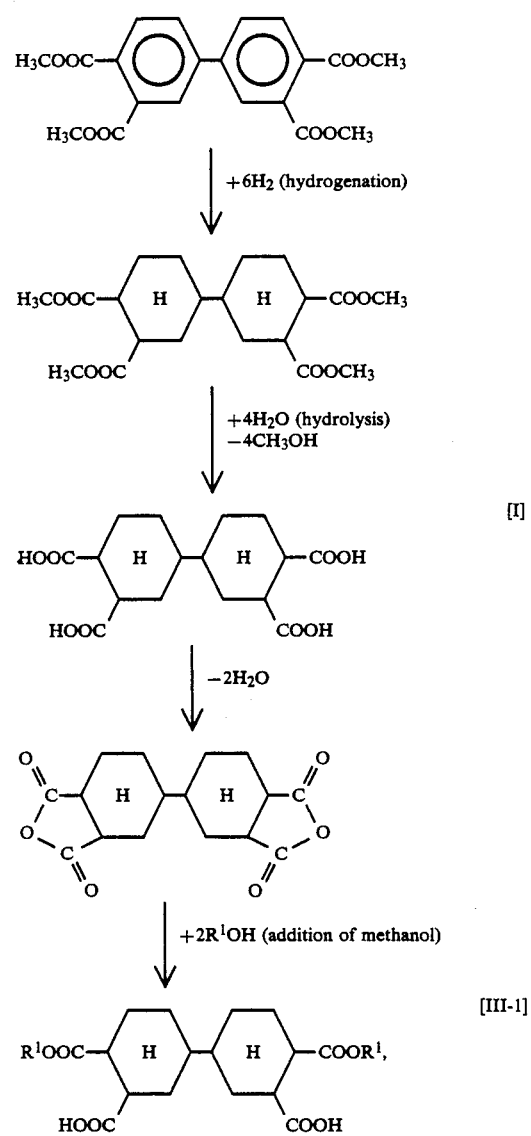

-continued

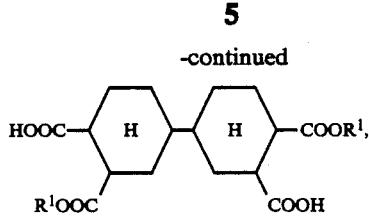
[III-2]

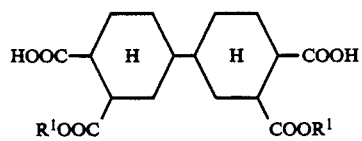
[III-3]

In the formulae [III-1] to [III-3], $R^1$ is an aliphatic group preferably having 1 to 4 carbon atoms such as $C_{1-4}$ alkyl, etc.

The present inventors had studied the process described in J. Org. Chem. vol. 31, p. 3438 (1966) for synthesizing dicyclohexyl-3,3',4,4'-tetracarboxylic acid. That is, an aqueous solution of biphenyl-3,4,3',4'-tetracarboxylic acid was hydrogenated in the presence of a rhodium catalyst. Since biphenyl-3,4,3',4'-tetracarboxylic acid is insoluble in water and causes a heterogeneous system reaction, the hydrogen pressure was raised to 50 kg/cm² and the reaction temperature was raised to 150° C., but no reaction took place. Further, when biphenyl-3,4,3',4'-tetracarboxylic acid was dissolved in a potassium hydroxide solution and subjected to hydrogenation using a rhodium catalyst, the reaction did not proceed. When biphenyl-3,4,3',4'-tetracarboxylic dianhydride was dissolved in acetic anhydride and subjected to hydrogenation similarly, the reaction did not proceed.

The compounds of the formulae [I], [II], [III-1], [III-2] and [III-3] can be represented by the formula:

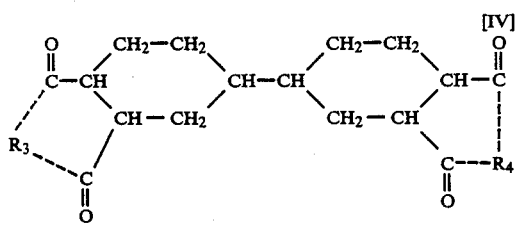
[IV]

wherein $R_3$ and $R_4$ are independently an oxygen atom, two hydroxyl groups or $C_{1-4}$ alkoxy groups or a combination of a hydroxyl group and an alkoxy group preferably having 1 to 4 carbon atoms.

A polyamide-acid or polyamide-acid ester having repeating units represented by at least one of the formulae [VI], [VII] and [VIII] can be produced by reacting the compound of the formula [IV] with a diamine of the formula:

, $H_2N-R_2-NH_2$    [V]

wherein $R_2$ is a bivalent group such as an aliphatic group having 2 or more carbon atoms, an alicyclic or aromatic group having 6 or more carbon atoms, etc., which may contain one or more oxygen atoms, sulfur atoms or silicon atoms.

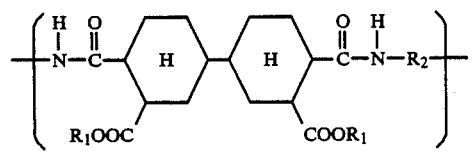
[VI]

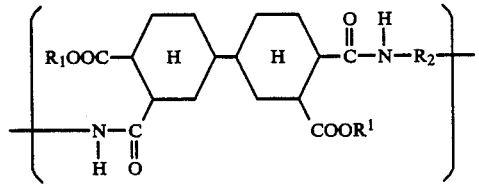
[VII]

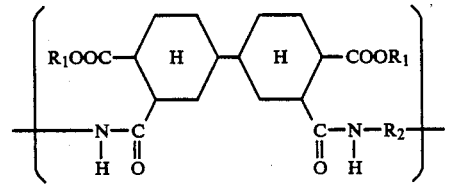
[VIII]

wherein $R_1$ is hydrogen or a monovalent hydrocarbon group having 1 to 4 carbon atoms such as $C_{1-4}$ alkyl; and $R_2$ is as defined above.

The bivalent group of $R_2$ in the formulae [VI], [VII] and [VIII] in the polyamide-acid or polyamide-acid ester corresponds to the $R_2$ in the diamine of the formula [V]. That is, $R_2$ is determined by the kind of diamine. Therefore, a polymide having repeating units of the formula:

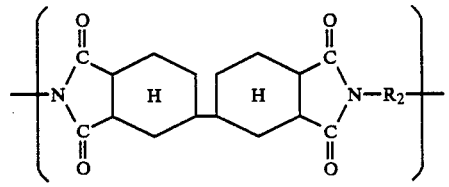
[IX]

wherein $R_2$ is as defined above, obtained from the polyamide-acid or polyamide-acid ester also has $R_2$ which corresponds to the $R_2$ in the diamine of the formula [V]. That is, $R_2$ is determined by the kind of diamine.

Examples of the diamine of the formula [V] are aromatic diamines such as 4,4'-diaminodiphenyl ether, 4,4'-diaminodiphenylmethane, 4,4'-diaminodiphenylsulfone, 4,4'-diaminodiphenylsulfide, benzidine, m-phenylenediamine, p-phenylenediamine, 2,2-bis(4-aminophenyl)propane, diaminobenzophenone, 1,5-diaminonaphthalene, 2,6-diaminonaphthalene, 1,3-bis(4-aminophenoxy)benzene, 1,4-bis(4-aminophenoxy)benzene, 4,4'-di(4-aminophenoxy)-diphenylsulfone, 4,4'-bis(3-aminophenoxy)diphenylsulfone, 4,4'-di(3-aminophenoxy)diphenylsulfone, 2,2-bis[4-(4-aminophenoxy)phenyl]propane, 4,4''-diamino-p-terphenyl, etc.

It is also possible to use diamines such as ethylenediamine, 1,3-propanediamine, tetramethylenediamine, pentamethylenediamine, hexamethylenediamine, heptamethylenediamine, octamethylenediamine, 1,4-diaminocyclohexane, 1,2-bis(4-aminophenoxy)ethane, bis[2-(4-aminophenoxy)ethyl]ether, 1,2-bis[2-(4-aminophenoxy)-ethoxy]ethane, bis{2-[2-(4-aminophenoxy)e- thoxy]ethyl}ether, 4,4'-diaminodiphenyl ether-3-sulfoneamide, 3,4'-diaminodiphenyl ether-4-sulfoneamide, 3,4'-diaminodiphenyl ether-3'-sulfoneamide, 3,3'-diaminodiphenyl ether-4-sulfoneamide, 4,4'-diaminodiphenylmethane-3-sulfoneamide, 3,4'-diaminodiphenylmethane-4-sulfoneamide, methane-4-sulfoneamide, 3,4'-diaminodiphenylmethane-3'-sulfoneamide, 3,3'-diaminodiphenylmethane-4-sulfoneamide, 4,4'-diaminodiphenylsulfone-3-sulfoneamide, 3,4'-diaminodiphenylsulfone-4-sulfoneamide, 3,4'-diaminodiphenylsulfone-3'-sulfoneamide, 3,3'-diaminodiphenylsulfone-4-sulfoneamide, 4,4'-diaminodiphenylsulfide-3-sulfoneamide, 3,4'-diaminodiphenylsulfide-4-sulfoneamide, 3,3'-diaminodiphenylsulfide-4-sulfoneamide, 3,4'-diaminodiphenylsulfide-3'-sulfoneamide, 1,4-diaminobenzene-2-sulfoneamide, 4,4'-diaminodiphenyl ether-3-carbonamide, 3,4'-diaminodiphenyl ether-4-carbonamide, 3,4'-diaminodiphenyl ether-3'-carbonamide, 3,3'-diaminodiphenyl ether-4-carbonamide, 4,4'-diaminodiphenylmethane-3-carbonamide, 3,4'-diaminodiphenylmethane-4-carbonamide, 3,4'-diaminodiphenylmethane-3'-carbonamide, 3,3'-diaminodiphenylmethane-4-carbonamide, 4,4'-diaminodiphenylsuflone-3-carbonamide, 3,4'-diaminodiphenylsulfone-4-carbonamide, 3,4'-diaminodiphenylsulfone-3'-carbonamide, 3,3'-diaminodiphenylsulfone-4-carbonamide, 4,4'-diaminodiphenylsulfide-3-carbonamide, 3,4'-diaminodiphenylsulfide-4-carbonamide, 3,3'-diaminodiphenylsulfide-4-carbonamide, 3,4'-diaminodiphenylsulfide-3'-sulfoneamide, 1,4-diaminobenzene-2-carbonamide, etc. From the viewpoint of improving heat resistance, the use of aromatic diamines and diaminoamide compounds is preferable.

In order to improve the adhesive properties of the orientation film in the liquid crystal display device, it is preferable to co-use diaminosiloxane represented by the formula:

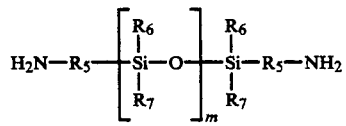
[X]

wherein R is a bivalent aliphatic or aromatic hydrocarbon group preferably having 3 to 8 carbon atoms such as a propylene group, a phenylene group, etc.; $R_6$ and $R_7$ are independently a monovalent hydrocarbon group having 1 to 6 carbon atoms such as an alkyl group preferably having 1 to 6 carbon atoms, a phenyl group, etc.; and m is an integer of 1 or more.

Examples of the diaminosiloxane of the formula [X] are as follows:

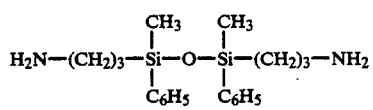

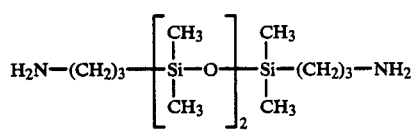

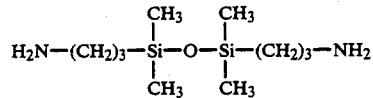

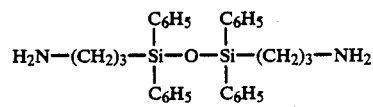

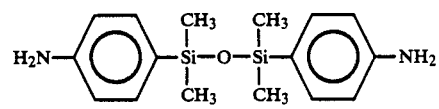

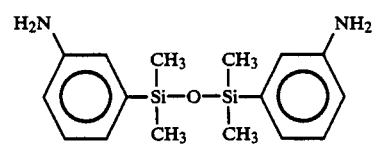

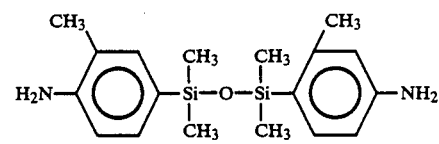

Since the total amount of the diamine of the formula [V] and the diaminosiloxane of the formula [X] and the amount of dicyclohexyl-3,4,3',4'-tetracarboxylic dianhydride make the molecular weight of the resulting polyamide-acid which is a precursor of polyimide larger, it is preferable to use them in almost equimolar amounts. In the production of polyamide-acid or polyamide-acid ester, it is preferable to use an inert solvent such as N-methyl-2-pyrrolidone, N,N-dimethylacetoamide, N,N-dimethylformamide, dimethylsulfoxide, hexamethylphosphoramide, tetramethylenesulfone, p-chlorophenol, p-bromophenol, 2-chloro-4-hydroxytoluene, etc. In the production of polyamide-acid having repeating units of the formulae [VI], [VII] and/or [VIII], a diamine of the formula [V] is dissolved in an inert solvent mentioned above, and dicyclohexyl-3,4,3',4'-tetracarboxylic dianhydride, which is one of compounds of the formula [IV], is added thereto, followed by stirring at a temperature preferably about 80° C. or lower, more preferably room temperature or lower. By this, the reaction is carried out immediately to gradually increase the viscosity of the reaction system for producing a polyamide-acid. After the reaction, in order to adjust the viscosity of polyamide-acid varnish, it is possible to add a Cellosolve series solvent such as diethylene glycol monomethyl ether, diethylene glycol monoethyl ether, ethylene glycol monobutyl ether, etc. in addition to the solvent used for the reaction.

In order to obtain a polyamide-acid ester having repeating units of the formulae [VI], [VII] and/or [VIII], the carboxylic acid groups of the polyamide-acid synthesized as mentioned above are changed to acid chloride moieties using thionyl chloride or the like, followed by the reaction with an alcohol such as methanol, ethanol, etc. Or, dicyclohexyl-3,4,3',4'-tetracarboxylic acid or the like is changed to an acid chloride as mentioned above, followed by esterification. It is also possible to obtain the polyamide-acid ester by ring opening dicyclohexyl-3,4,3',4'-tetracarboxylic dianhydride with an alcohol to give diesterified product, which is then reacted with a diamine in a solvent.

When $R_1$ in the formulae [VI], [VII] and [VIII] is a monovalent hydrocarbon group, the R corresponds to the alcohol used for obtaining the above-mentioned polyamide-acid ester. That is, R is the moiety obtained by the hydroxyl group from the alcohol.

In order to convert the polyamide-acid or polyamide-acid ester to polyimide, it is preferable to conduct a heat treatment at 100° to 300° C. for 30 minutes to 5 hours. In the case of the polyamide-acid, the polyimide having the repeating units of the formula [IX] is obtained by dehydration and ring closure. In the case of the polyamide-acid ester, the polyimide having the repeating units of the formula [IX] is obtained by removal of alcohol and ring closure. As agents for removing water or alcohol, it is possible to use acetic anhydride, phosphoric acid, or the like. In such a case, it is possible to use an organometallic or amine series catalyst such as dibutyl tin dilaurate triethylamine or the like. By this, the reaction proceeds to increase the viscosity of the reaction system and finally to produce the polyimide.

As mentioned above, the polyimide can be obtained at a lower temperature. Further the obtained polyimide is good in transparency, heat resistance and mechanical properties, so that it can be used for covering semiconductors and the like, in optical devices as well as conventional uses. In addition, the polyimide having the repeating units of the formula [IX] is particularly useful as an orientation film in liquid crystal display devices.

The orientation film can be obtained by using the polyimide of the present invention as follows. The polyamide-acid is dissolved in a solvent to give a solution of solid content of 0.01 to 40%. As the solvent, there can be used dimethyl formamide, dimethyl acetamide, dimethyl sulfoxide, N-methylpyrrolidone, ethylene glycol n-butyl ether, diethylene glycol monoethyl ether, etc. The thus obtained solution is coated on a substrate having transparent electrodes thereon by a conventional method such as a dip method, a spin coating method, a spray method, a printing method, a brushing method, or the like, followed by heat treatment at 100° C. to 250° C. The polyamide-acid is subjected to dehydration ring closure to give a polyimide film. The polyimide film is subjected to rubbing at one direction to give the orientation film.

A pair of thus obtained substrates having said electrodes and orientation films are placed in opposition to each other so that their respective orientation films will face each other, and then they are bonded to each other in a way to form a predetermined space therebetween by interposing a spacer between them or by other means. A conventional liquid crystal composition is poured into said space and then the pouring opening is closed. In this way, a liquid crystal display device of this invention can be obtained.

The tilt angle between the orientation film of this invention and the liquid crystal is very large. Therefore, the orientation film of this invention can be advantageously used not only for the SBE-type liquid crystal display devices but also for the TN-type liquid crystal display devices.

The thus obtained orientation film for liquid crystal display device is excellent in transparencey, and adhesion to the substrate, and can be produced by a low temperature heat treatment (lower than 300° C.), so that the liquid crystal display device thus obtained is excellent in liquid crystal orientation controlling power and reliability for a long period of time. Further, workability for producing the liquid crystal display device is improved. Therefore, the liquid crystal display element using the polyimide having the repeating units of the formula [IX] as an orientation film can be used for a color filter dyed with gelatin, a thin film transistor using amorphous silicon, etc. Further, it becomes possible to produce liquid crystal display elements wherein an element or part having lower heat resistance is used, e.g. a plastic film is used in place of a glass plate.

This invention is illustrated by way of the following Examples, in which all parts and percents are by weight unless otherwise specified.

EXAMPLE 1

(1) Preparation of dicyclohexyl-3,4,3',4'-tetracarboxylic acid tetramethyl ester In a 500-ml autoclave equipped with a magnetic up-and-down stirring device, 38.6 g (0.100 mole) of biphenyl-3,4,340 ,4'-tetracarboxylic acid tetramethyl ester, 193 g of tetrahydrofran and 3.86 g of a catalyst obtained by carrying 5% of rhodium on activated carbon (mfd. by Nippon Engelhard Ltd.) were placed. Hydrogenation was carried out under a hydrogen pressure of 30 kg/cm$^2$ at a reaction temperature of 100° C. After 3.5 hours, the consumption of hydrogen was stopped. The consumed hydrogen amount obtained from a reduced value of hydrogen pressure in a bomb was 98.7% based on the theoretical consumed hydrogen amount (0.60 mole).

After removing the rhodium catalyst carried on the activated carbon by filtration, the tetrahydrofuran used as a solvent was removed by evaporation to yield 36.87 g (0.0925 mole) of dicyclohexyl-3,4,3',4'-tetracarboxylic acid tetramethyl ester as a white waxy material.

Analysis by $^1$H-NMR (HITACHI R-250 Nuclear Magnetic Resonance Spectrometer mfd. by Hitachi, Ltd.) revealed that the hydrogenation was completed, since no benzene nuclear hydrogen nor hydrogen attached to carbon-carbon double bonds was found.

(2) Preparation of dicyclohexyl-3,4,3',4'-tetracarboxylic acid

In a 1-liter egg-plant type flask equipped with a condenser, 29.9 g (0.075 mole) of dicyclohexyl-3,4,3',4'-tetracarboxylic acid tetramethyl ester was placed, and 200 g of methanol was added thereto to give a uniform solution After adding 200 g of a 10% sodium hydroxide solution thereto, the flask was placed in an oil bath of 100° C. and subjected to reflux for 6 hours. Then, the methanol was removed by evaporation. After concentrating the reaction solution to 140 g, 48 ml of 36% hydrochloric acid was added thereto to make the pH 1. The reaction solution was clouded white at pH 4–5 and precipitated a white fine powder at pH 1. The precipitate was taken out by filtration, washed with water and dried to give 17.8 g (0.052 mole) of white fine powdery crystals of dicyclohexyl-3,4,3',4'-tetracarboxylic acid.

Figure 2:
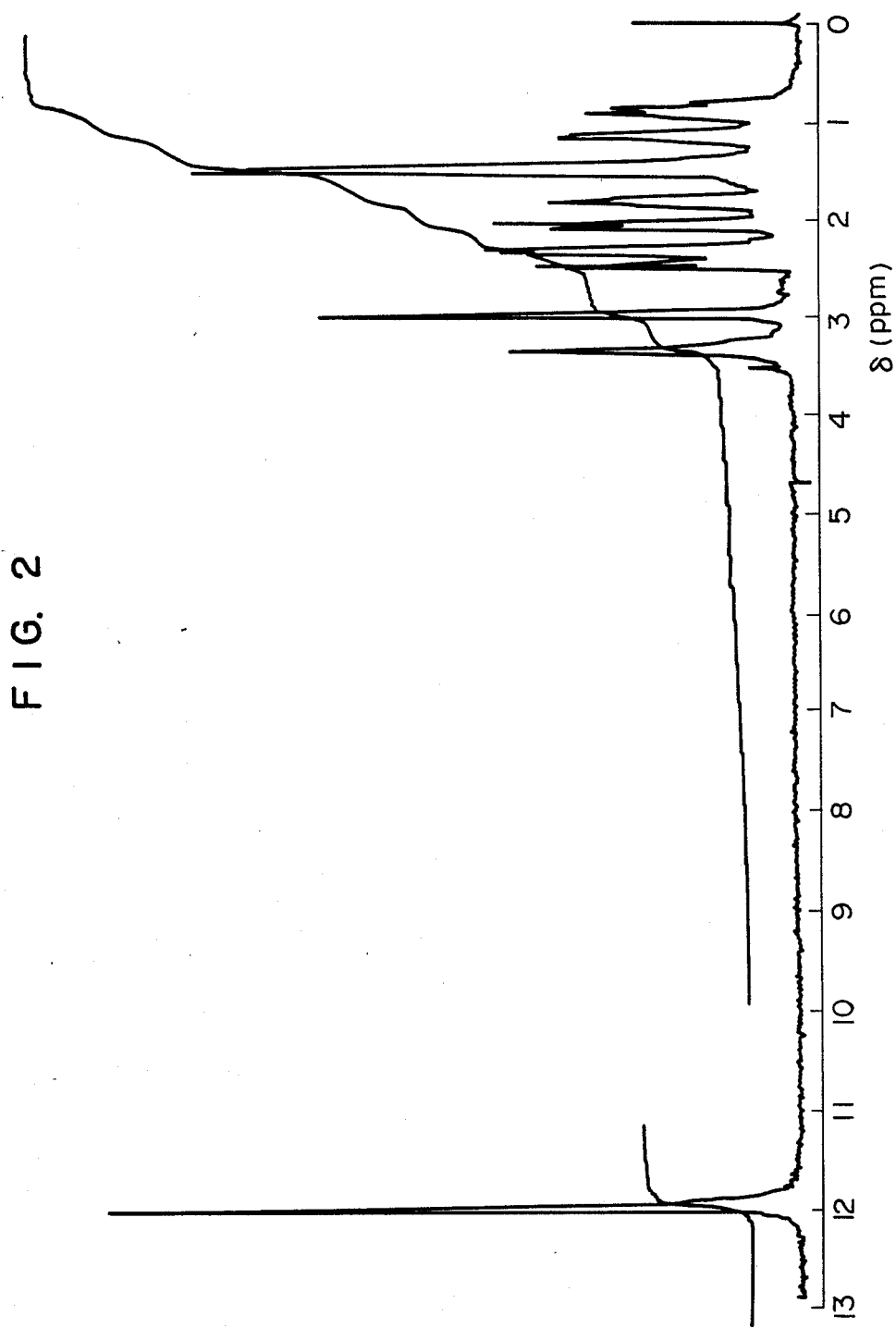
FIG. 2 is $^1$H-NMR spectrum of dicyclohexyl-3,4,3',4'-tetracarboxylic acid.

Infrared spectrum of these crystals is shown in FIG. 1 (measured by using HITACHI 260-30 type Infrared Spectrophotometer mfd. by Hitachi, Ltd., and the KBr method). $^1$H-NMR spectrum of these crystals is shown in FIG. 2, wherein the absorption at 2.50 ppm is due to the solvent d$_6$-dimethylsulfoxide and the absorption at 3.35 ppm is due to water contained in the solvent In the absorptions removing the above-mentioned two absorptions, an integrated intensity ratio of an absorption at 11.95 ppm due to a carboxyl group proton to an absorption at 0.87-3.00 ppm due to a cyclohexane ring proton is 29:132 (=4:18.2), which is in good agreement to the theoretical value (the compound of the formula [I]). These crystals had a melting point of 219° to 222° C.

Elementary Analysis

|  | C (%) | H (%) |
|---|---|---|
| Found | 56.24 | 6.53 |
| Calculated | 56.13 | 6.48 |

(3) Preparation of dicyclohexyl-3,4,3',4'-tetracarboxylic acid dianhydride

In a 300-ml egg-plant type flask equipped with a condenser, 15.0 g (0.044 mole) of dicyclohexyl-3,4,3',4'-tetracarboxylic acid and 180 g of acetic anhydride were placed. The flask was placed in an oil bath heated at 150° C. and subjected to reflux for 1 hour. Then, the reaction solution was filtered while hot. The filtrate was allowed to stand for cooling to deposit white crystals. The crystals were taken out by filtration and dried under a pressure of 30 mm Hg at 100° C. for 2 hours to give 10.8 g (0.035 mole) of crystals having a melting point of 231° to 234° C.

Elementary Analysis Compound of the Formula [II])

|  | C (%) | H (%) |
|---|---|---|
| Found | 62.59 | 6.01 |
| Calculated | 62.74 | 5.92 |

Figure 3:
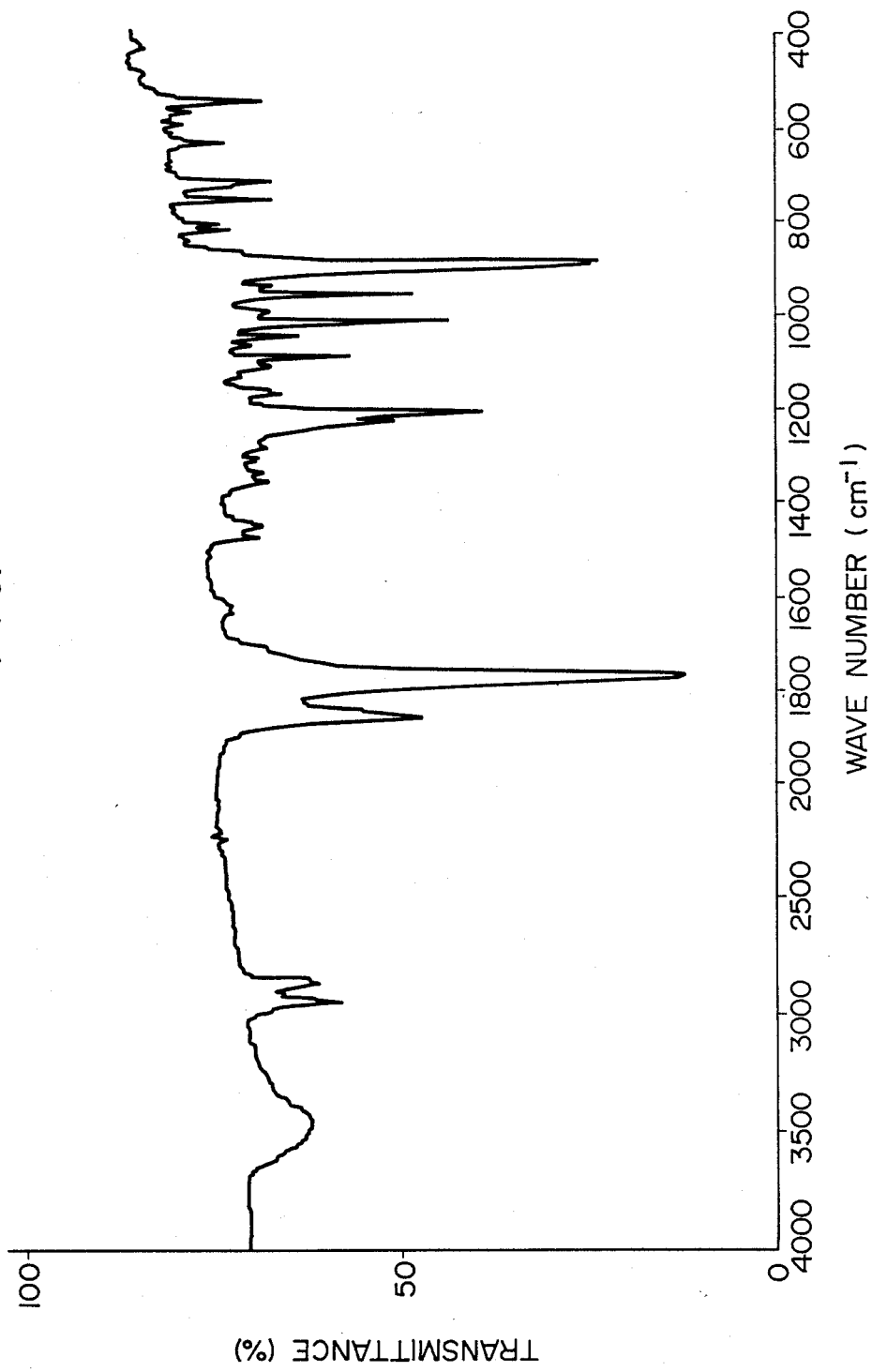
FIG. 3 is an infrared spectrum of dicyclohexyl-3,4,3',4'-tetracarboxylic dianhydride.
Figure 4:
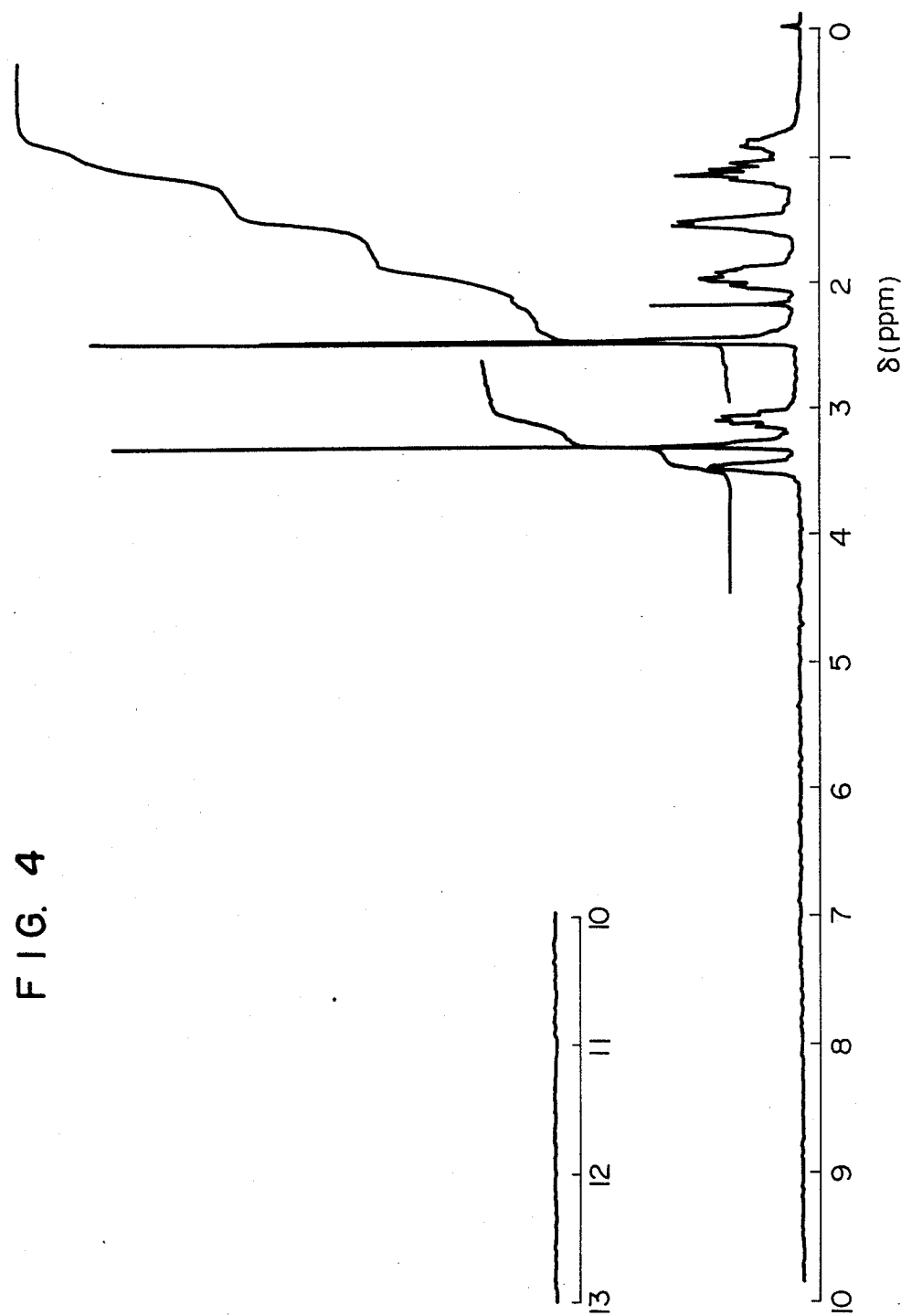
FIG. 4 is $^1$H-NMR spectrum of dicyclohexyl-3,4,3',4'-tetracarboxylic dianhydride.

FIG. 3 shows an infrared spectrum of these crystals. FIG. 4 shows a $^1$H-NMR spectrum of these crystals. In FIG. 4, there is no absorption of carboxylic acid proton at low magnetic field of 10-13 ppm. This means that an anhydride is obtained.

COMPARATIVE EXAMPLE 1

In the same 500-ml autoclave as used in Example 1, 250 ml of deionized water, 20.0 g of biphenyl-3,4,3',4'-tetracarboxylic acid and 4.0 g of the rhodium catalyst used in Example 1 were placed. Stirring was continued under a hydrogen pressure of 50 kg/cm$^2$ at 150° C. for 5 hours. But no consumption of hydrogen was admitted and no reaction proceeded.

COMPARATIVE EXAMPLE 2

A uniform solution was obtained by adding 30.0 g (0.102 mole) of biphenyl-3,4,3',4'-tetracarboxylic dianhydride to an aqueous solution of 350 g of deionized water and 25.6 g (0.387 mole) of potassium hydroxide, followed by reflux. The resulting aqueous solution had a pH of 7.6.

In the same 500-ml autoclave as used in Example 1, 250 g of aqueous solution of biphenyl-3,4,3',4'-tetracarboxylic acid potassium salt (18.5 g as biphenyl-3,4,3',4'-tetracarboxylic dianhydride) and 1.85 g of the rhodium catalyst used in Example 1 were placed. Stirring was continued under a hydrogen pressure of 35 kg/cm$^2$ at 130° C. for 5 hours. But no consumption of hydrogen was admitted and no reaction proceeded.

COMPARATIVE EXAMPLE 3

To 250 g of acetic anhydride, 10.0 g of biphenyl-3,4,3',4'-tetracarboxylic dianhydride was added and refluxed with heating for 1 hour, followed by gradual cooling to room temperature. Deposited biphenyl-3,4,3',4'-tetracarboxylic dianhydride was removed by filtration and the whole amount of the filtrate was placed in the same 500-ml autoclave as used in Example 1. The deposited amount of biphenyl-3,4,3',4'-tetracarboxylic dianhydride was 6.47 g after dried and the amount placed in the autoclave was 3.53 g. To the autoclave, 1.76 g of the rhodium catalyst used in Example 1 was placed. Stirring was continued under a hydrogen pressure of 31 kg/cm$^2$ at 102° C. for 5 hours. But no consumption of hydrogen was admitted and no reaction proceeded.

EXAMPLE 2

Figure 5:
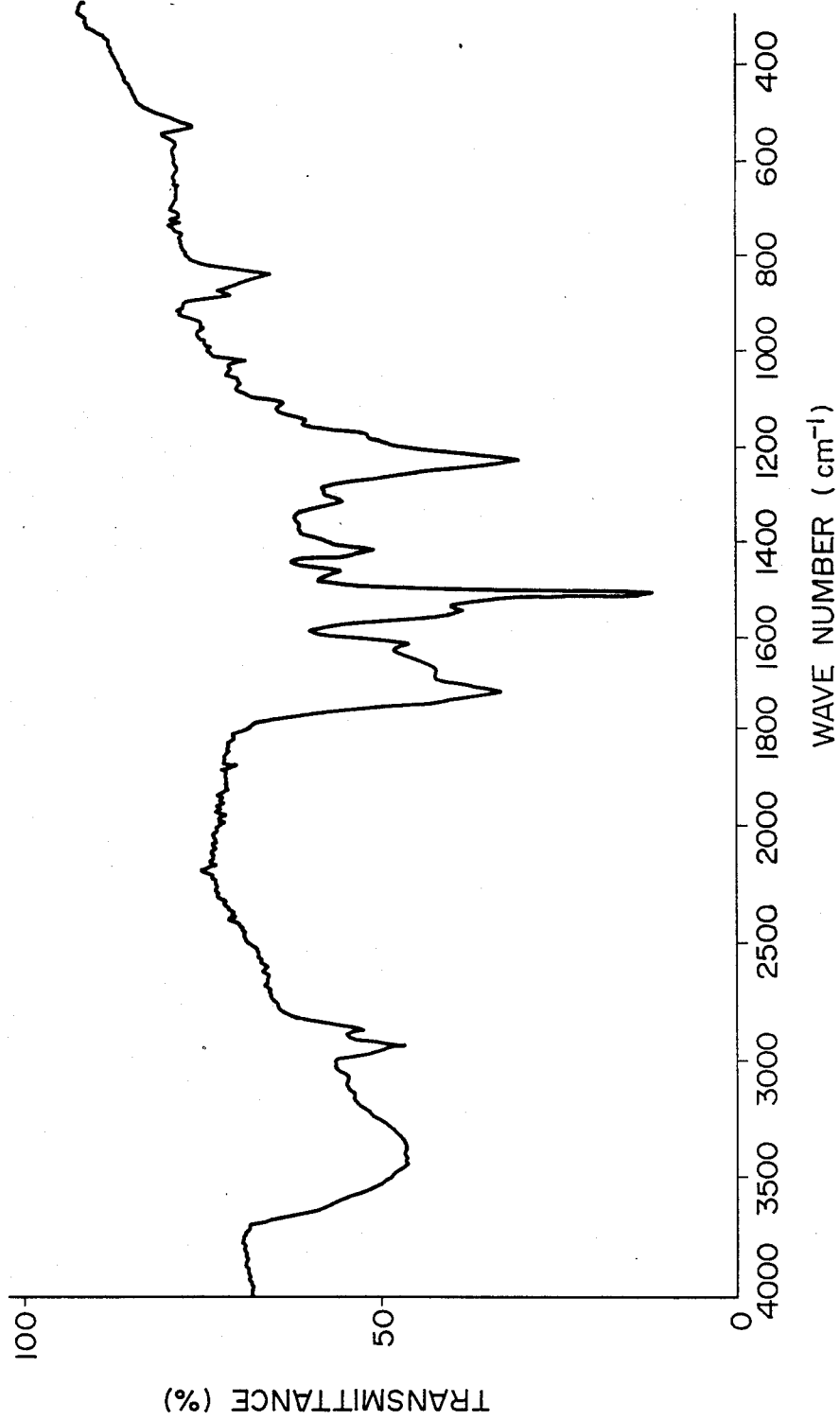
FIG. 5 is an infrared spectrum of a polyamide-acid obtained by reacting dicyclohexyl-3,4,3',4'-tetracarboxylic dianhydride with 4,4'-diaminodiphenyl ether in Example 2.

In a 200-ml three-necked flask equipped with a thermometer, a stirrer and a calcium chloride tube, 12.014 g (60 mmoles) of 4,4'-diaminodiphenyl ether and 70.92 g of N-methyl-2-pyrrolidone as a solvent were placed and dissolved with stirring at room temperature. To this, 18.379 g (60 mmoles) of dicyclohexyl-3,4,3',4'-tetracarboxylic dianhydride was added and stirred at room temperature for 8 hours. With the lapse of time, the viscosity of polyamide-acid reaction solution increased and became 86 poises at 25° C. after stirring for 8 hours. Then, the reaction solution was heated (cooked) at 80° C. for about 5 hours to adjust the viscosity to 15 poises, followed by coating on a glass plate and drying. A part of the resulting polyamide-acid was sampled. FIG. 5 shows an infrared spectrum of this polyamide-acid (measured by using HITACHI 270-50 type infrared spectrophotometer mfd. by Hitachi, Ltd. and the KBr method).

Figure 6:
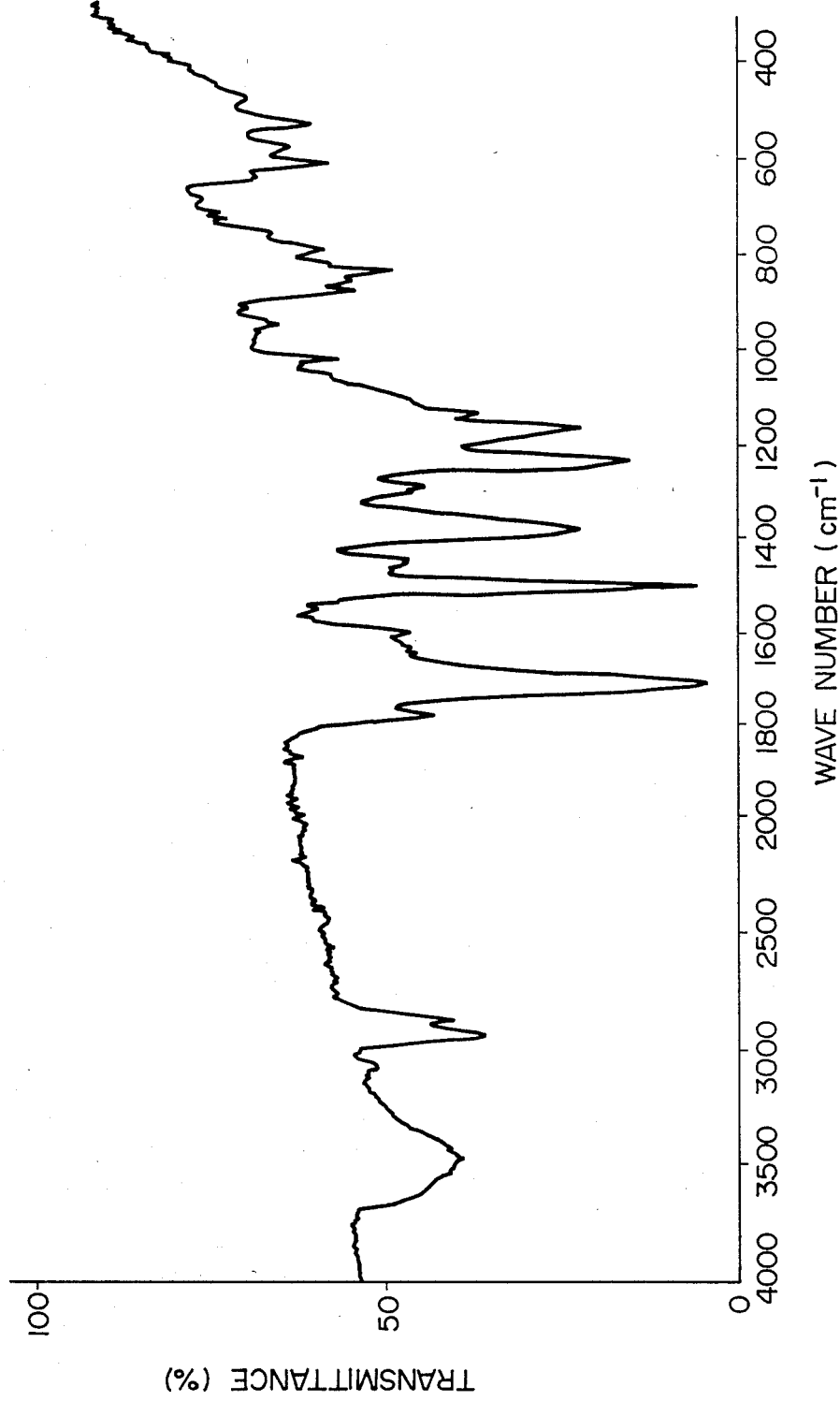
FIG. 6 is an infrared spectrum of a polyimide obtained by heat treating the polyamide-acid obtained in Example 2 at 250° C.

The polyamide-acid obtained by coating on the glass plate and dried was subjected to heat treatment at 250° C. for 1 hour. After peeling from the glass plate, there was obtained a polyimide film of 35 μm thick with good transparency. A part of the polyimide film was sampled and subjected to the measurement of infrared spectrum (shown in FIG. 6). The glass transition temperature (Tg) measured by using a 910 type differential scanning calorimeter (mfd. by E. I. du Pont de Nemours & Co.) was 244° C.

Properties of the polyimide film were measured and evaluated as follows.

Test Methods (1) Pyrolysis temperature

A film of 10 mg was subjected to measurement using a thermobalance (910 type differential scanning calorimeter, mfd. by E. I. du Pont de Nemours & Co.) at a temperature rise rate of 5° C./min in an air stream. The temperature at 5% weight loss was defined as the pyrolysis temperature.

(2) Transmission

Visible light transmission at wavelengths of 700 nm, 600 nm and 500 nm was measured using a spectrophotometer (HITACHI 200-20 type Double Beam Spectrophotometer mfd. by Hitachi, Ltd.).

The results were shown in Table 1.

EXAMPLE 3

The process of Example 2 was repeated except for using 19.463 g (45 mmoles) of 4,4'-di(3-aminophenoxy)-diphenylsulfone, 13.784 g (45 mmoles) of dicyclohexyl-3,4,3',4'-tetracarboxylic dianhydride, and 77.58 g of N-methyl-2-pyrrolidone to produce a polyamide-acid solution and a polyimide film.

Properties of the polyimide film were measured in the same manner as described in Example 2 and shown in Table 1.

COMPARATIVE EXAMPLE 4

The process of Example 2 was repeated except for using 8.010 g (40 mmoles) of 4,4'-diaminodiphenyl ether, 8.725 g (40 mmoles) of pyromellitic dianhydride and 94.83 g of N-methyl-2-pyrrolidone to give a polyamide-acid solution, followed by heat treatment at 350° C. for 1 hour to give a polyimide film.

Properties of the polyimide film were measured in the same manner as described in Example 2 and shown in Table 1.

COMPARATIVE EXAMPLE 5

The process of Example 2 was repeated except for using 15.018 g (75 mmoles) of 4,4'-diaminodiphenyl ether, 14.860 g (75 mmoles) of 1,2,3,4-butanetetracarboxylic dianhydride and 69.72 g of N-methyl-2-pyrrolidone to give a polyamide-acid solution and a polyimide film.

Properties of the polyimide film were measured in the same manner as described in Example 2 and shown in Table 1.

COMPARATIVE EXAMPLE 6

1,2,4,5-Cyclohexanetetracarboxylic acid was synthesized by the process described in J. Org. Chem. vol. 31, p. 3438 (1966), followed by dehydration ring closure using acetic anhydride to give 1,2,4,5-cyclohexanetetracarboxylic dianhydride. A polyamide-acid solution was prepared in the same manner as described in Example 2 except for using 15.692 g (70 mmoles) of 1,2,4,5-cyclohexanetetracarboxylic dianhydride, 14.017 g (70 mmoles) of 4,4'-diaminodiphenyl ether, and 69.321 g of N-methyl-2-pyrrolidone. The polyamide-acid solution was coated on a glass plate, dried and subjected to a heat treatment at 250° C. for 1 hour. The coating was cracked like scales and not able to give a film.

coated on glass substrates having a pattern of indium tin oxide (ITO) transparent electrodes thereon. After coating, curing was conducted with heating at 200° C. for 1 hour to form a polyimide film of 1000 Å thick. The obtained films were excellent in transparency.

The obtained films were subjected to a rubbing treatment with a piece of gauze at a predetermined direction. A pair of thus treated electrode substrates were placed in parallel with a certain gap and sealed with an epoxy series sealant. A Schiff's base type liquid crystal composition was poured into the space thus formed from an inlet and sealed. Both outer sides of the resulting cell were adhered to a pair of polarizing plates to give a liquid crystal display device.

Orientation properties of the resulting display device was good. Further, when exposed to an atmosphere of 70° C. with 95% RH for 100 hours, no change was found in display properties of the device and no display nonuniformity such as blurring took place.

EXAMPLE 5

A polyamide-acid was obtained by dissolving 19.5 g (0.045 mole) of 4,4'-bis(3-aminophenoxy)diphenylsulfone and 1.2 g (0.005 mole) of 1,3-bis(aminopropyl)-tetramethyldisiloxane in 84 g of N-methyl-2-pyrrolidone and reacting with 15.3 g (0.05 mole) of dicyclohexyl-3,3,4,3',4'-tetracarboxylic dianhydride at room temperature for 6 hours.

The resulting solution was adjusted to have a solid content of 15% with N-methyl-2-pyrrolidone. A polyimide film was obtained in the same manner as described in Example 4. The obtained film was excellent in transparency.

Using the polyimide film thus obtained, a liquid crystal display device was produced in the same manner as described in Example 4.

Orientation properties of the resulting display device was good. Further, when exposed to an atmosphere of 70° C. with 95% RH for 100 hours, no change was found in display properties of the device and no display nonuniformity such as blurring took place.

TABLE 1

| Example No. | Polyamide-acid solution | | Polyimide film (35 μ thick) | | | | |
|---|---|---|---|---|---|---|---|
| | Non-volatile content (%) | Reached viscosity (poise) | Film formation | Pyrolysis temperature (°C.) | Visible light transmission (%) | | |
| | | | | | 700 nm | 600 nm | 500 nm |
| Example 2 | 30 | 86 | Good | 463 | 87 | 85 | 83 |
| Example 3 | 30 | 64 | Good | 452 | 88 | 87 | 84 |
| Comparative Example 4 | 15 | 1950 | Good | 529 | 82 | 73 | 39 |
| Comparative Example 5 | 30 | 145 | Good | 425 | 89 | 88 | 85 |
| Comparative Example 6 | 30 | 520 | Bad | 382 | — | — | — |

EXAMPLE 4

In a 200-ml four-necked flask equipped with a thermometer, a stirrer and a calcium chloride tube, 12 g (0.06 mole) of 4,4'-diaminodiphenyl ether, and 71 g of N-methyl-2-pyrrolidone were placed and stirred at room temperature for dissolving. To this, 18 g (0.06 mole) of dicyclohexyl-3,4,3',4'-tetracarboxylic dianhydride was added to carrying the reaction at room temperature for 8 hours to give a polyamide-acid.

The resulting solution was adjusted to have a solid content of 15% with N-methyl-2-pyrrolidone and spin

COMPARATIVE EXAMPLE 7

The process of Example 4 was repeated except for using 10 g (0.05 mole) of 4,4'-diaminodiphenyl ether, 10.9 g (0.05 mole) of pyromellitic dianhydride and 118 g of N-methyl-2-pyrrolidone to give a polyamide-acid solution and a polyimide film. The obtained polyimide film was colored.

COMPARATIVE EXAMPLE 8

1,2,4,5-Cyclohexanetetracarboxylic dianhydride was obtained by synthesizing 1,2,4,5-cyclohexanetetracarboxylic acid according to the process disclosed in J. Org. Chem. vol. 31, p. 3438 (1966), followed by dehydration ring closure using acetic anhydride.

A polyamide-acid solution was prepared in the same manner as described in Example 4 except for using 15.7 g (0.07 mole) of 1,2,4,5-cyclohexanetetracarboxylic dianhydride, 14 g (0.07 mole) of 4,4-diaminodiphenyl ether and 70 g of N-methyl-2-pyrrolidone. The polyamide-acid solution was coated on glass substrates in the same manner as described in Example 4 and heat treated at 250° C. for 1 hour to give a polyimide film. When the rubbing treatment was carried out by using a piece of gauze, the polyimide film was injured due to poor film strength.

COMPARATIVE EXAMPLE 9

A polyamide-acid solution was obtained in the same manner as described in Example 4 except for using 15 g (0.075 mole) of 4,4'-diaminodiphenyl ether, 14.9 g (0.075 mole) of 1,2,3,4-butanetetracarboxylic dianhydride and 70 g of N-methyl-2-pyrrolidone. The polyamide-acid solution was coated on glass substrates in the same manner as described in Example 4 and heat treated at 250° C. for 1 hour to give a polyimide film. When the rubbing treatment was carried out by using a piece of gauze, the polyimide film was injured due to poor film strength.

What is claimed is:

1. Dicyclohexyl-3,4,3',4'-tetracarboxylic acid.

2. Dicyclohexyl-3,4,3',4'-tetracarboxylic dianhydride.

3. A process for producing dicyclohexyl-3,3,4,3',4'-tetracarboxylic acid which comprises hydrogenating biphenyl-3,4,3',4'-tetracarboxylic acid tetramethyl ester using a rhodium catalyst, followed by hydrolysis.

4. A process according to claim 3, wherein the biphenyl-3,4,3',4'-tetracarboxylic acid tetramethyl ester is first dissolved in an organic solvent and the hydrogenation is carried out under a hydrogen pressure of 2 to 100 kg/cm² at room temperature to 150° C.

5. A process for producing dicyclohexyl-3,4,3'4'-tetracarboxylic dianhydride which comprises hydrogenating biphenyl-3,4,3',4'-tetracarboxylic acid tetramethyl ester using a rhodium catalyst, followed by hydrolysis to give dicyclohexyl-3,4,3',4'-tetracarboxylic acid, and subjecting the dicyclohexyl-3,4,3',4'-tetracarboxylic acid to dehydration ring closure.

6. A polyamide-acid or a polyamide-acid ester having repeating units represented by at least one of the following formulae:

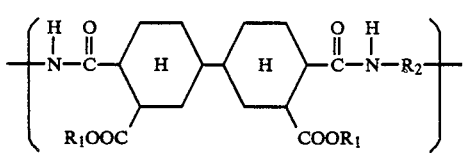

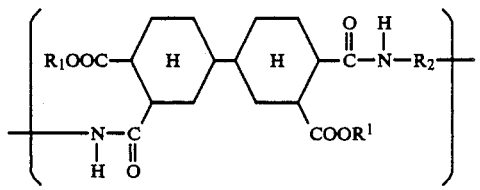

and

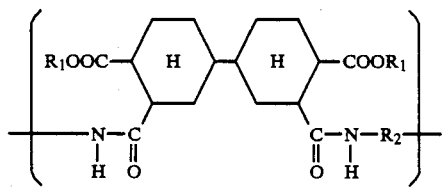

wherein $R_1$ is hydrogen or a monovalent hydrocarbon group; and $R_2$ is a bivalent group.

7. A process for producing a polyamide-acid or a polyamide-acid ester having repeating units represented by at least one of the following formulae:

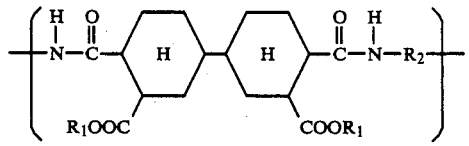

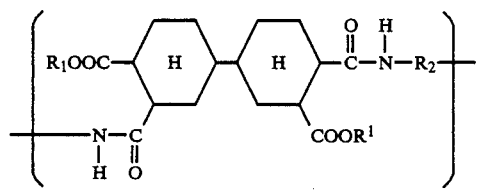

and

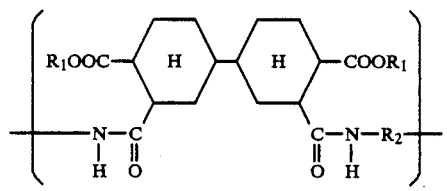

wherein R is hydrogen or a monovalent hydrocarbon group; and $R_2$ is a bivalent group, which comprises reacting a compound of the formula:

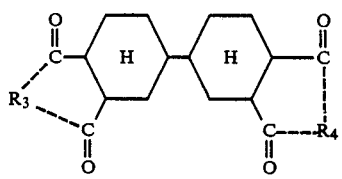

wherein R and $R_4$ are independently an oxygen atom, two hydroxyl groups or a combination of a hydroxyl group and an alkoxy group, with a diamine of the formula:

$H_2N-R_2-NH_2$ wherein $R_{22}$ is as defined above.

8. A polyamide having repeating units of the formula:

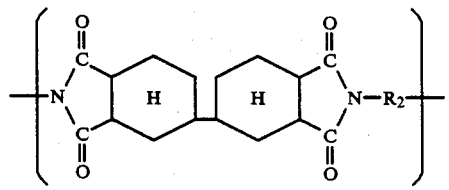

wherein $R_2$ is a bivalent group.

9. A process for producing a polyimide having repeating units of the formula:

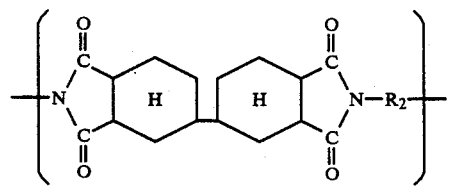

wherein $R_2$ is a bivalent group, which comprises subjecting a polyamide-acid or a polyamide-acid ester having repeating units represented by at least one of the following formulae:

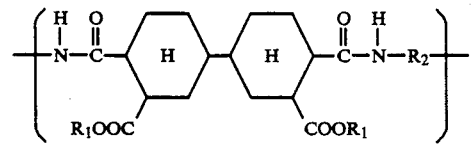

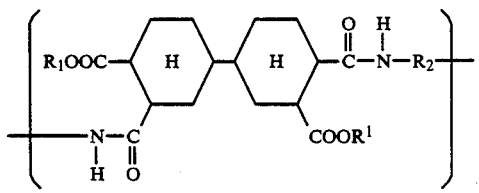

and

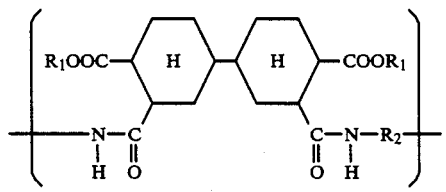

wherein $R_1$ is hydrogen or a monovalent hydrocarbon group; and $R_2$ is a vibalent group, to dehydration or alcohol removal reaction for ring closure.

10. An orientation film for a liquid crystal display device made from a polyimide having repeating units of the formula:

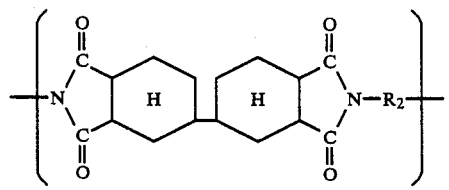

wherein $R_2$ is a bivalent group.

11. In a liquid crystal display device comprising a pair of substrates formed thereon transparent electrodes and orientation films formed on the substrates, the improvement wherein the orientation films are made from a polyimide having repeating units of the formula:

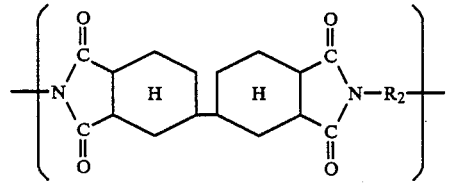

wherein $R_2$ is a bivalent group.

* * * * *